(12) United States Patent
Wu et al.

(10) Patent No.: US 7,723,302 B2
(45) Date of Patent: May 25, 2010

(54) METHOD OF TREATING PARKINSON'S DISEASE

(75) Inventors: Jang-Yen Wu, Boca Raton, FL (US); Dipnarine Maharaj, Boynton Beach, FL (US)

(73) Assignee: Florida Atlantic University, Boca Raton, FL (US)

( * ) Notice: Subject to any disclaimer, the term of this patent is extended or adjusted under 35 U.S.C. 154(b) by 0 days.

(21) Appl. No.: 12/113,723

(22) Filed: May 1, 2008

(65) Prior Publication Data
US 2008/0300176 A1  Dec. 4, 2008

Related U.S. Application Data

(60) Provisional application No. 60/915,336, filed on May 1, 2007.

(51) Int. Cl.
*A61K 38/19* (2006.01)
*C07K 14/535* (2006.01)

(52) U.S. Cl. ...................................................... 514/12
(58) Field of Classification Search .................. None
See application file for complete search history.

(56) References Cited

U.S. PATENT DOCUMENTS

| | | | |
|---|---|---|---|
| 2002/0198150 A1* | 12/2002 | Chajut | 514/12 |
| 2004/0141946 A1* | 7/2004 | Schaebitz et al. | 424/85.1 |
| 2006/0263332 A1 | 11/2006 | Li et al. | |
| 2007/0015206 A1* | 1/2007 | Gebbink et al. | 435/7.1 |
| 2007/0031373 A1* | 2/2007 | Lopez et al. | 424/85.1 |
| 2009/0170752 A1* | 7/2009 | Lopez et al. | 514/8 |

OTHER PUBLICATIONS

Meuer 2006 (Journal of Neurochemistry 97:675-686).*
Teshima 1997 (Cytokines, Cellular and Molecular Therapy 3:101-114).*
Arvidsson, A. et al., Neuronal replacement from endogenous precursors in the adult brain after stroke. Nat. Med. 8, 963-970, 2002.
Baker, S.A. et al., Dopaminergic nigrostriatal projections regulate neural precursor proliferation in the adult mouse subventricular zone. Eur. J. Neurosci. 20, 575-579, 2004.
Benraiss, A. et al., Adenoviral brain derived neurotrophic factor induces both neostriatal and olfactory neuronal recruitment from endogenous progenitor cells in the adult forebrain. J. Neurosci. 21, 6718-6731, 2001.
Bertilsson, G. et al. Peptide hormone exendin-4 stimulates subventricular zone neurogenesis in the adult rodent brain and induces recovery in an animal model of parkinson's disease. J Neurosci Res 86, 326-338, 2008.
Bjugstad, K.B. et al., Human neural stem cells migrate along the nigrostriatal pathway in a primate model of Parkinson's disease. Exp Neurol. 211, 362-369, 2008.
Borlongan, C.V. et al., New hope for stroke patients: mobilization of endogenous stem cells. CMAJ 174, 954-955, 2006.
Burgess, A.W. et al., Characterization of a serum factor stimulating the differentiation of myelomonocytic leukemic cells. Int. J. Cancer 26, 647-654, 1980.
Cao, X Q et al., Recombinant human granulocyte colony-stimulating factor protects against MPTP-induced dopaminergic cell death in mice by altering Bc1-2/Bax expression levels, J Neurochem 99, 861-867, 2006.
Demetri, G.D. et al., Granulocyte colony-stimulating factor and its receptor, Blood 78, 2791-2808, 1991.
Espejo, E.F. et al., Adrenergic hyperactivity and metanephrine excess in the nucleus accumbens after prefrontocortical dopamine depletion. J Neurophysiol 85, 1270-1274, 2001.
Fallon, J. et al., in vivo induction of massive proliferation, directed migration, and differentiation of neural cells in the adult mammalian brain. Proc Natl Acad Sci U S A. 97, 14686-14691, 2000.
Freundlieb, N. et al., Dopaminergic substantia nigra neurons project topographically organized to the subventricular zone and stimulate precursor cell proliferation in aged primates. J. Neurosci. 26, 2321-2325, 2006.

(Continued)

*Primary Examiner*—Daniel E. Kolker
(74) *Attorney, Agent, or Firm*—Novak Druce + Quigg LLP; Gregory A. Nelson; Amy A. Dobbelaere

(57) ABSTRACT

The invention relates to the discovery that in an animal model of Parkinson's disease (PD), administration of granulocyte colony-stimulating factor (G-CSF) to rodents having 1-methyl-4-phenyl-1,2,3,6-tetrahydropyridine (MPTP)-induced PD restored the function of dopamine neurons. In these animals, G-CSF treatment increased the number of dopamine neurons in the substantia nigra (SN), G-CSF treatment partially restored the nigrostriatal pathway, and G-CSF restored the function of dopamine to the level before MPTP treatment. The invention also relates to the discovery that treatment of a human patient with corticobasilar ganglionic degeneration, a rare progressive neurological disorder characterized by Parkinsonism and coritcal dysfunction, with G-CSF resulted in a significant improvement in the patient's Unified Parkinson's Disease Rating Scale evaluations as well as measures of activity of daily living. The invention further relates to the discovery that G-CSF treatment of a patient who had suffered an acute stroke resulted in a significant improvement in neurological function, the patient having minimal observable disability seven years later. The methods described herein can be used to treat PD in a mammalian subject (e.g., rodent, human) as well as other neurodegenerative diseases such as Alzheimer's disease, spinal cord injury, and stroke.

8 Claims, 13 Drawing Sheets

OTHER PUBLICATIONS

Frielingsdorf, H. et al., No evidence for new dopaminergic neurons in the adult mammalian substantia nigra. Proc Natl Acad Sci U S A. 101, 10177-10182, 2004.

Gibson, C.L. et al., G-CSF reduces infarct volume and improves functional outcome after transient focal cerebral ischemia in mice. J Cereb Blood Flow Metab 25, 431-439, 2005.

Grigg, A. P. et al., Optimizing dose and scheduling of filgrastim (granulocyte colony-stimulating factor) for mobilization and collection of peripheral blood progenitor cells in normal volunteers Blood 86, 4437-4445, 1995.

Hoglinger, G. U. et al., Dopamine depletion impairs precursor cell proliferation in Parkinson disease. Nat Neurosci. 7, 726-735, 2004.

Horner, P. J. et al., Regenerating the damaged central nervous system. Nature 407, 963-970, 2000.

Jackson-Lewis, V. et al., Protocol for the MPTP mouse model of Parkinson's disease. Nat Protoc. 2, 141-151, 2007.

Jordan, J.D. et al., Adult neurogenesis as a potential therapy for neurodegenerative diseases. Discov Med. 6, 144-147, 2006.

Kay, J. N. et al., Differential response of ventral midbrain and striatal progenitor cells to lesions of the nigrostriatal dopaminergic projection. Dev Neurosci. 22, 56-67, 2000.

Komine-Kobayashi, M. et al., Neuroprotective effect of recombinant human granulocyte colonystimulating factor in transient focal ischemia of mice. J Cereb Blood Flow Metab 26, 402-413, 2006.

Kucia, M. et al., a population of very small embryonic-like (VSEL) CXCR4(+)SSEA-1 (+)Oct-4+ stem cells identified in adult bone marrow. Leukemia 20, 857-869, 2006.

Lee, S. T. et al., Granulocyte-colony stimulating factor attenuates striatal degeneration with activating survival pathways in 3-nitropropionic acid model of Huntington's disease. Brain Res 1194, 130-137, 2008.

Lie, D. C. et al., the Adult Substantia Nigra Contains Progenitor Cells with Neurogenic Potential. J. Neurosci. 22, 6639-6649, 2002.

Lu, C. Z. et al., Neuroprotection of G-CSF in cerebral ischemia. Front Biosci 12, 2869-2875, 2007.

Luzzati, F. et al., Adult Neurogenesis and Local Neuronal Progenitors in the Striatum. Neurodegener Dis 4, 322-327, 2007.

Magavi, S. S. et al., Induction of neurogenesis in the neocortex of adult mice. Nature 405, 951-955, 2000.

Mao, L. et al., Profound astrogenesis in the striatum of adult mice following nigrostriatal dopaminergic lesion by repeated MPTP administration. Brain Res Dev Brain Res. 131, 57-65, 2001.

Ming, G. L. et al., Adult neurogenesis in the mammalian central nervous system. Annu Rev Neurosci 28, 223-250, 2005.

Peng, J. et al., Fibroblast growth factor 2 enhances striatal and nigral neurogenesis in the acute 1-methyl-4-phenyl-1, 2, 3, 6-tetrahydropyridine model of Parkinson's disease. Neuroscience 153, 664-670, 2008.

Rascol, O. et al., Limitations of current Parkinson's disease therapy. Ann Neurol 53, S3-15, 2003.

Rousselet, E. et al., Behavioral changes are not directly related to striatel monoamine levels, number of nigral neurons, or dose of parkinsonian toxin MPTP in mice. Neurobiol Dis 14, 218-228, 2003.

Schabitz, W.R. et al., Neuroprotective effect of granulocyte colony-stimulating factor after focal cerebral ischemia. Stroke. 34, 745-751, 2003.

Schneider, A., et al., A role for G-CSF (granulocyte-colony stimulating factor) in the central nervous system. Cell Cycle. 4, 1753-1757, 2005.

Schneider, A. et al., the hematopoietic factor G-CSF is a neuronal ligand that counteracts programmed cell death and drives neurogenesis, J. Clin. Investigation, 115:8, 2083-2098, Aug. 2005.

Sedelis, M. et al., Behavioral phenotyping of the MPTP mouse model of Parkinson's disease. Behav Brain Res. 125, 109-125, 2001.

Shan, X. et al., Enhanced de novo neurogenesis and dopaminergic neurogenesis in the substantia nigra of MPTP-induced Parkinson's disease-like mice. Stem Cells 24, 1280-1287, 2006.

Shyu, W. et al., Functional Recovery of Stroke Rats Induced by Granulocyte Colony-Stimulating Factor-Stimulated Stem Cells, Circulation, 1847-1854, Sep. 28, 2004.

Stroncek, D.F. et al. Treatment of normal individuals with granulocyte-colony-stimulating factor: donor experiences and the effects on peripheral blood CD34+ cell counts and on the collection of peripheral blood stem cells . . . Transfusion 36, 601-610, 1996.

Van Kampen, J. M., et al., Dopamine D3 receptor agonist delivery to a model of Parkinson's disease restores the nigrostriatal pathway and improves locomotor behavior. J Neurosci. 26, 7272-7280, 2006.

Wu et al., Mechanism and therapy of granulocyte colony-stimulating factor (G-CSF) in Parkinson's Disease, J. Neurochemistry, 104 (Suppl.1), 148, 2008.

Zhao, C. et al., Mechanisms and functional implications of adult neurogenesis. Cell 132, 645-660, 2008.

Zhao, M. et al., Evidence for neurogenesis in the adult mammalian substantia nigra. Proc Natl Acad Sci U S A. 100, 7925-7930, 2003.

* cited by examiner

METHOD OF TREATING PARKINSON'S DISEASE

CROSS-REFERENCE TO RELATED APPLICATION

The present application claims the priority of U.S. Provisional Application No. 60/915,336 filed May 1, 2007, which is incorporated herein in its entirety by reference.

FIELD OF THE INVENTION

The invention relates to the fields of molecular biology and medicine. More particularly, the invention relates to methods for treating neurodegenerative diseases including Parkinson's disease and stroke in mammalian subjects.

BACKGROUND

Neuronal death plays a critical role in most of the important neural pathologies, including stroke, epilepsy, Parkinson's disease (PD) and Alzheimer's disease. PD is a progressive neurodegenerative disease affecting about 1% of people over the age of 50. Its symptoms include slowness of movement, difficulty in initiating willed movements, rigidity and tremors. At the cellular level, it is characterized by a massive loss of dopamine (DA) neurons in the brain. Unfortunately, a cure does not yet exist for PD. Current treatments for mitigating the progression and symptoms of PD include levodopa combined with carbidopa, anti-cholinergic drugs, brain surgery, tissue transplant, and stem cell therapies currently under investigation.

SUMMARY

The invention relates to the discovery that in an animal model of PD, administration of granulocyte colony-stimulating factor (G-CSF) to rodents having 1-methyl-4-phenyl-1,2,3,6-tetrahydropyridine (MPTP)-induced PD restored the function of dopamine neurons. In these animals, G-CSF treatment increased the number of dopamine neurons in the substantia nigra (SN), G-CSF treatment partially restored the nigrostriatal pathway, and G-CSF enhanced the function of dopamine neurons (e.g., an increase in stimulation-induced release of dopamine). The invention also relates to the discovery that treatment of a human patient with corticobasilar ganglionic degeneration, a rare progressive neurological disorder characterized by Parkinsonism and coritcal dysfunction, with G-CSF resulted in a significant improvement in the patient's Unified Parkinson's Disease Rating Scale (UPDRS) evaluations as well as measures of daily living activities. The invention further relates to the discovery that G-CSF treatment of a patient who had suffered an acute stroke resulted in a significant improvement in neurological function, the patient having minimal observable disability. The methods described herein can be used to treat PD in a mammalian subject (e.g., rodent, human) and other neurodegenerative diseases including stroke.

Accordingly, the invention features a method of treating Parkinson's disease or stroke in a mammal. The method includes the steps of: (a) providing a composition including recombinant human G-CSF; and (b) administering the composition to a mammalian subject having Parkinson's disease or to a mammalian subject that has experienced a stroke, wherein administering the composition to the mammalian subject replenishes dopaminergic neuron loss in the brain of the mammalian subject. In the method, administering the composition to the mammalian subject results in increased levels of dopaminergic neurons and increased levels of dopaminergic neuronal function in the brain of the mammalian subject. In the method, administering the composition to the mammalian subject results in restoration of nigrostriatal pathway in the brain of the mammalian subject. In the method, administering the composition to the mammalian subject can result in recruitment of stem cells to the brain of the mammalian subject.

In one example of the method, the composition is administered to a mammalian subject that has experienced a stroke, and administration of the composition results in an increased number of neurons and an increase in neuronal function in the mammalian subject.

In the method, a composition can include at least one pharmaceutically acceptable carrier or diluent. The composition can be administered to the mammalian subject once a day at a dose of about 480 μg to about 960 μg.

Unless otherwise defined, all technical terms used herein have the same meaning as commonly understood by one of ordinary skill in the art to which this invention belongs.

As used herein, "protein" or "polypeptide" are used synonymously to mean any peptide-linked chain of amino acids, regardless of length or post-translational modifications, e.g., glycosylation or phosphorylation. A "purified" polypeptide is one that is substantially separated from other polypeptides in a cell or organism in which the polypeptide naturally occurs (e.g., 30, 40, 50, 60, 70, 80, 90, 95, 96, 97, 98, 99, 100% free of contaminants).

By the terms "recombinant G-CSF," "rG-CSF" or "recombinant G-CSF protein" is meant an expression product of a cloned G-CSF gene.

When referring to a nucleic acid molecule or polypeptide, the term "native" refers to a naturally-occurring (e.g., a wild-type; "WT") nucleic acid or polypeptide.

As used herein, "Parkinson's disease" and "PD" mean a disease characterized behaviorally by slowness of movement, rigidity, a low-frequency rest tremor, and difficulty with balance and pathologically by a significant degeneration of dopamine (DA) neurons in the substantia nigra pars compacta (SNC).

By the phrase "replenishes dopaminergic neuron loss in the brain" is meant producing a net increase of dopamine neurons resulting from either recruitment of new dopamine neurons through a stem cell mechanism or preventing additional loss of dopamine neurons through a neuro-protective mechanism or both.

By the term "stroke" is meant a sudden neurological affliction usually related to the disturbance of cerebral blood supply including thrombosis, hemorrhage or embolism.

Although compositions and methods similar or equivalent to those described herein can be used in the practice or testing of the present invention, suitable compositions and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
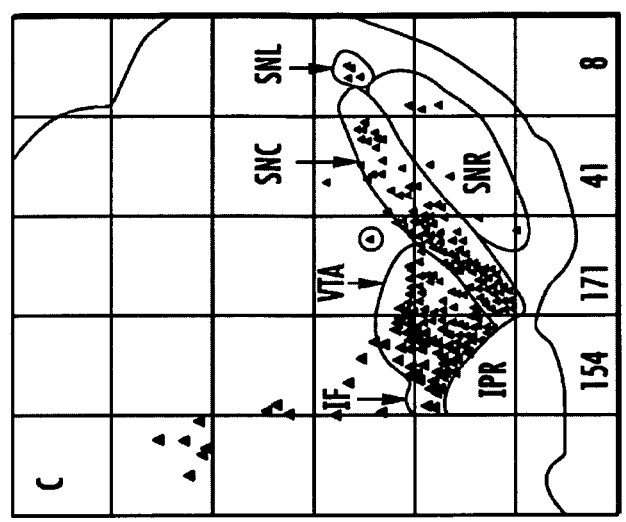
FIG. 1 is a pair of micrographs, a graph, and results from a cell counting analysis illustrating a marked loss of DA neurons in SNc in MPTP-treated mice as indicated by the loss of tyrosine hydroxylase (TH), a specific marker for DA neurons.
Figure 1:
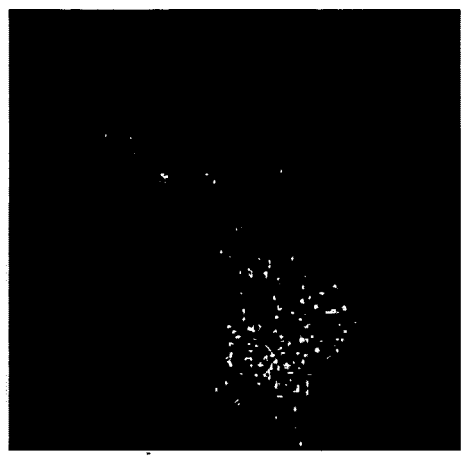
Figure 1:
Figure 1:
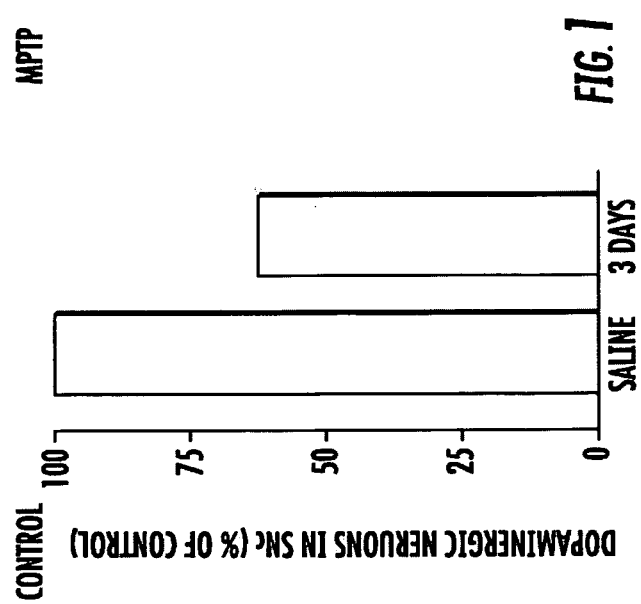

Described herein are methods for treating neurodegenerative diseases such as PD and stroke in a mammalian subject (e.g., rodent, human) that include administering a composition including G-CSF to the mammalian subject. The below described preferred embodiments illustrate adaptations of these methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 2003 (with periodic updates).

G-CSF

The methods described herein involve treating a mammalian subject (e.g., rodent, human) having PD or a mammalian subject having suffered from a stroke with a composition including G-CSF. G-CSF is a 19.6 KDa glycoprotein that has been used to treat several diseases and disorders including neutropenia, severe chronic neutropenia, acute leukemia, aplastic anemia, and myelodysplastic syndromes, as well as to mobilize peripheral blood stem cells prior to leukapheresis for bone marrow transplantation and to treat myelosuppression after transplantation. The receptor for G-CSF, G-CSFR (~140 KDa), is present in many tissues including the brain.

Any suitable source of G-CSF can be used to treat a mammalian subject. In the experiments described below, recombinant human G-CSF purchased from Amgen (NEUPOGEN® Amgen, Inc. Thousand Oaks, Calif.) was used. However, any commercially available G-CSF can be used in the methods described herein.

Administration of Compositions

The compositions described herein can be introduced into a cell or administered to a subject (e.g., a human) in any suitable formulation. For example, G-CSF may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions described herein may be administered to mammals by any conventional technique. Typically, such administration will be parenteral (e.g., intravenous, subcutaneous). The compositions may also be administered directly to a target site by, for example, surgical delivery to an internal or external target site, or by catheter to a site accessible by a blood vessel. The compositions may be administered in a single bolus, multiple injections, subcutaneously or by continuous infusion (e.g., intravenously or pump infusion). For parenteral administration, the compositions are preferably formulated in a sterilized pyrogen-free form.

Effective Doses

The compositions containing G-CSF are preferably administered to a mammal (e.g., rodent, human) in an effective amount, that is, an amount capable of producing a desirable result in a treated subject (e.g., restoring DA function). Such a therapeutically effective amount can be determined as described below.

Toxicity and therapeutic efficacy of the compositions utilized in the methods described herein can be determined by standard pharmaceutical procedures, using either cells in culture or experimental animals to determine the $LD_{50}$ (the dose lethal to 50% of the population). The dose ratio between toxic and therapeutic effects is the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of preferred compositions lies preferably within a range that includes an $ED_{50}$ with little or no toxicity. The dosage may vary within this range depending upon the dosage form employed and the route of administration utilized.

As is well known in the medical and veterinary arts, dosage for any one animal depends on many factors, including the subject's size, body surface area, age, the particular composition to be administered, time and route of administration, general health, and other drugs being administered concurrently. It is expected that an appropriate dosage for intravenous administration of a composition containing G-CSF would be in the range of about 5 μg/kg to about 32 μg/kg. As an example, for a 70 kg human, a 2 ml injection of 480 μg of G-CSF is presently believed to be an appropriate dose.

EXAMPLES

The present invention is further illustrated by the following specific examples. The examples are provided for illustration only and should not be construed as limiting the scope of the invention in any way.

Example 1

Mechanism and Therapy of G-CSF in an Animal Model of PD

Two mechanisms for the therapeutic effect of G-CSF are proposed. In the first mechanism, administration of G-CSF prevents further DA neuronal loss by inhibiting the apoptosis pathway through the interaction with G-CSF receptors in the DA neurons. It has been reported that G-CSF receptor is expressed in rodent dopaminergic substantia nigra neurons (Meuer et al., J. Neurochem. 97:675-686, 2006). In the second mechanism, administration of G-CSF replenishes the loss of DA neurons through mobilization of stem cells from central nervous system (CNS) and/or mobilization of the VSEL stem cells in the bone marrow and migration to the substantia nigra. Studies of G-CSF administration in normal donors show that G-CSF confers a significant increase in peripheral blood stem cell mobilization. VSEL stem cells were recently identified and shown to be present in adult bone marrow (Kucia et al., Leukemia 20:857-869, 2006).

Described herein is an animal model for PD in which peritoneal injection of 1-methyl-4-phenyl-1,2,3,6-tetrahydropyridine (MPTP), as described in the literature (Meuer et al., J Neurochem 97, 2006:675-686), induces a characteristic marked loss of DA neurons, as evidenced by the loss of TH-positive DA neurons in the substantia nigra area of the brain. To test the effect of G-CSF treatment on the mouse model of PD, different doses of G-CSF (50-250 μg/kg) were subcutaneously injected into mice that had received MPTP treatment as described above. Three parameters of DA function were determined: 1. The number of DA neurons as indicated from staining of TH, a specific marker of DA neuron; 2. Release of DA determined under non-stimulation and stimulation conditions using in vivo microdialysis; 3. Synaptic connectivity of DA system in nigra-striatal pathway using gold-labeled retrograde transport marker. In all three parameters measured as an index of function of DA neurons, G-CSF was found to restore the DA function in MPTP-treated animals to about the same level as the control group suggesting that G-CSF or similar stem cell-stimulating drugs may provide an effective treatment and restoration of lost functions in patients with PD.

Figure 2:
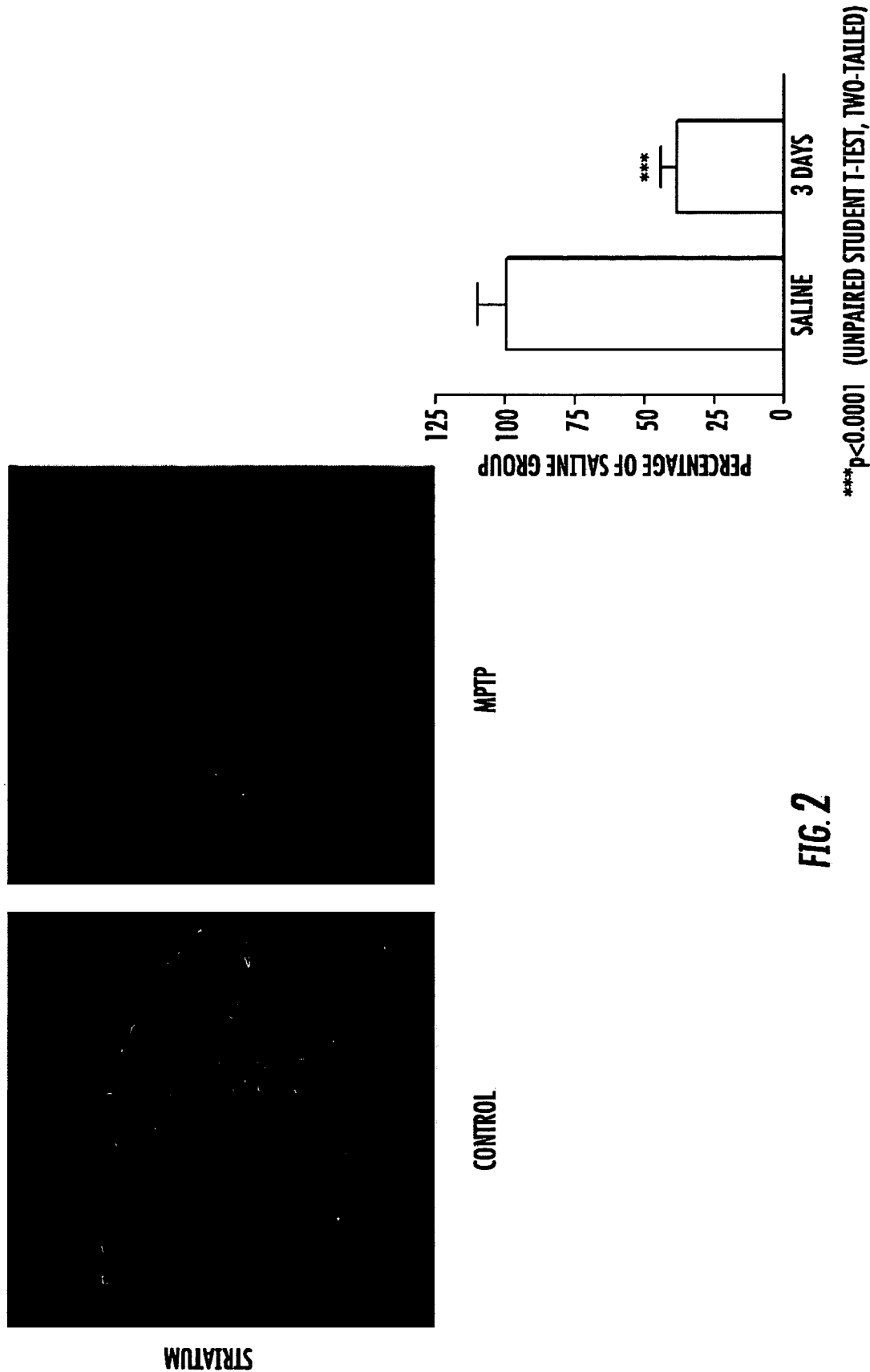
FIG. 2 is a pair of micrographs and a graph illustrating a massive loss (greater than 65%) of the nerve terminals of DA neurons in striatum after MPTP treatment.
Figure 3:
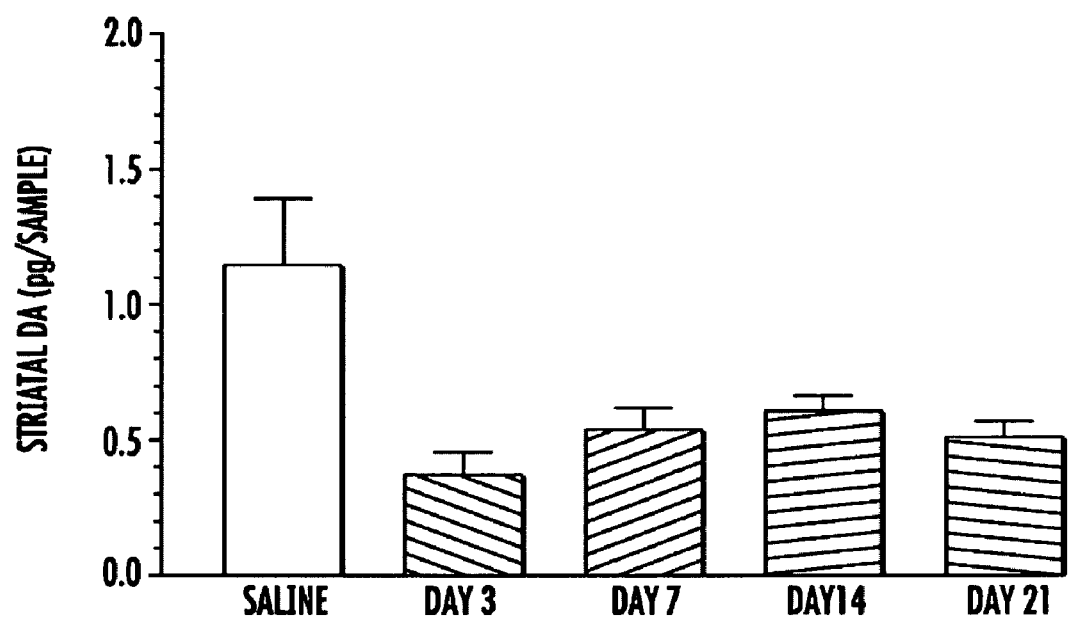
FIG. 3 is a graph showing dopamine levels in striatum are markedly reduced after MPTP treatment.
Figure 4:
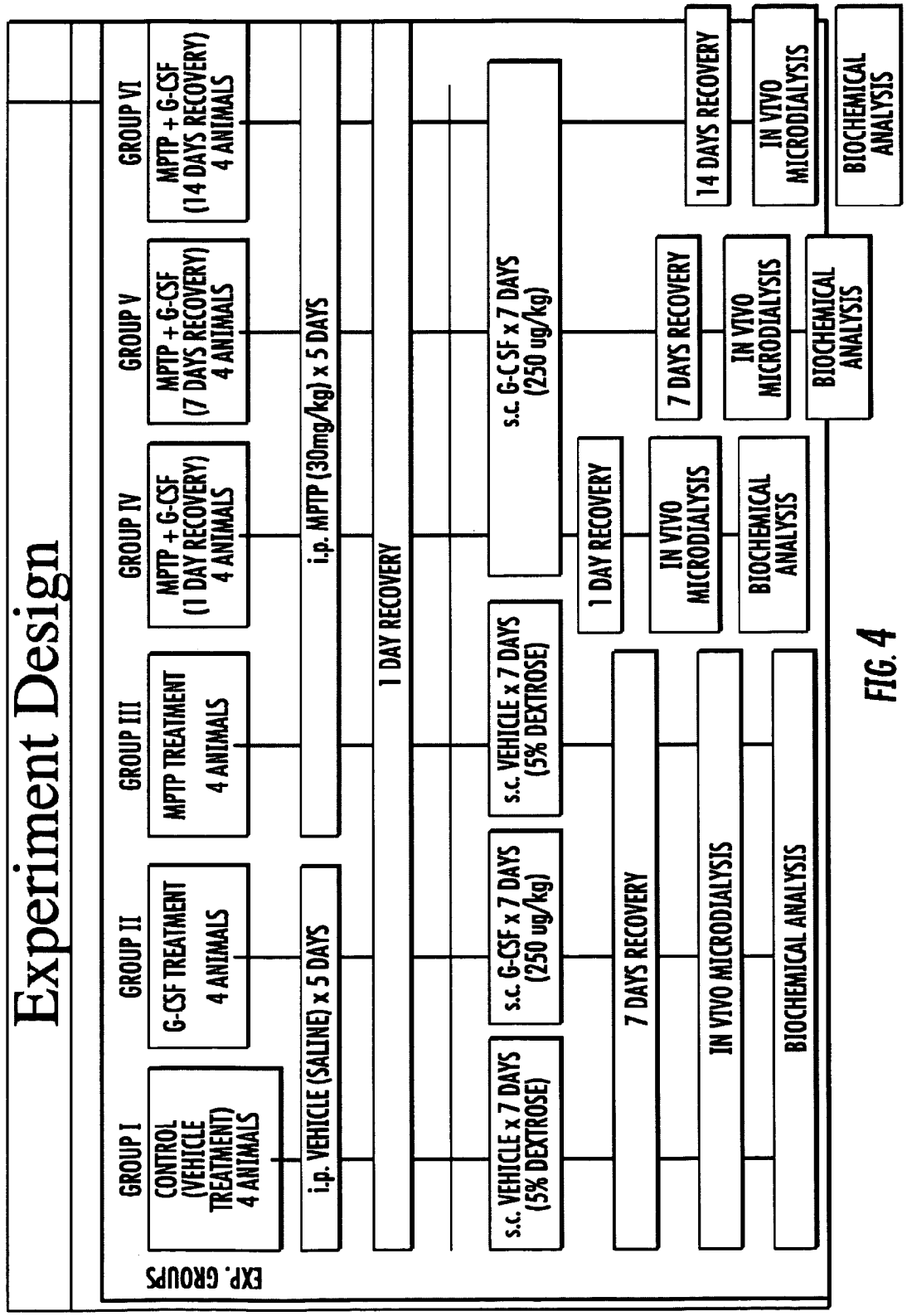
FIG. 4 is a schematic of the experimental design used to show the effect of G-CSF on DA system after MPTP-treatment.

FIGS. 1-3 show that MPTP-treated mice have the same biochemical characteristics as PD and can be used as an animal model for PD. FIGS. 1-3 show that mice injected with an intraperitoneal injection of MPTP (30 mg/kg) for 5 days developed biochemical characteristics of PD including a loss of about 40% of TH-positive, DA neurons in SNc (FIG. 1), a loss of 70% of TH-positive, DA neuronal process and terminals in the striatum (FIG. 2) and a loss of 70% of DA release in the striatum (FIG. 3). FIG. 4 illustrates the experimental protocol to test the effect of G-CSF in MPTP-induced PD animal model.

Figure 6A:
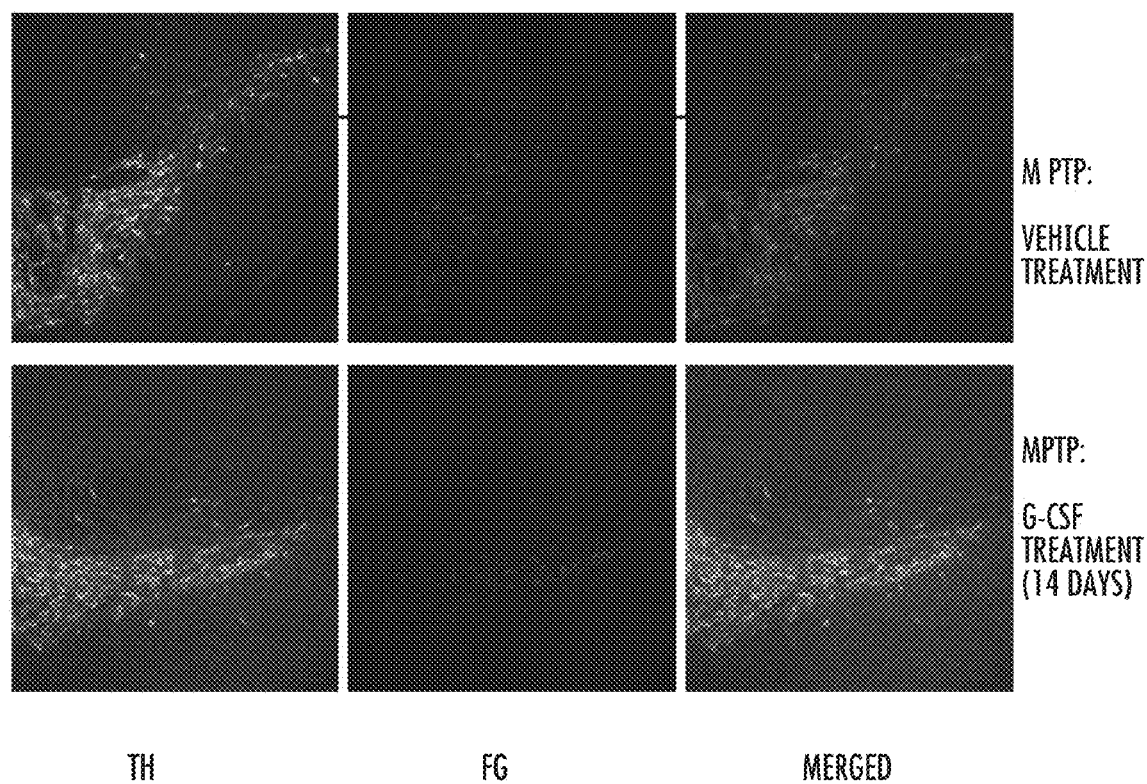
FIG. 6A is a series of representative micrographs depicting FluoroGold (FG) labeling in the SN 14 days after 5% dextrose+MPTP (top panel) or 5% dextrose+MPTP+G-CSF treatment (bottom panel) showing that G-CSF treatment has restored the nigro-striatum pathway from 40% to 70% as indicated in FG-positive tracing.
Figure 6B:
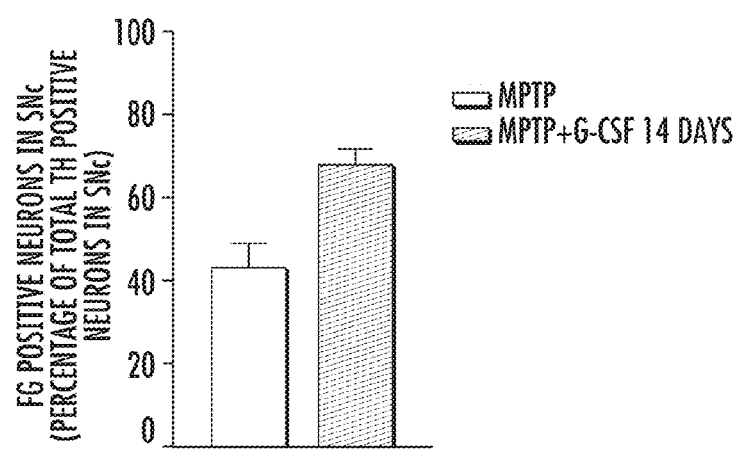
FIG. 6B is a graph showing the results of a quantitative analysis of FG-positive cells counted across 8 sections throughout SN. *p<0.01.
Figure 7:
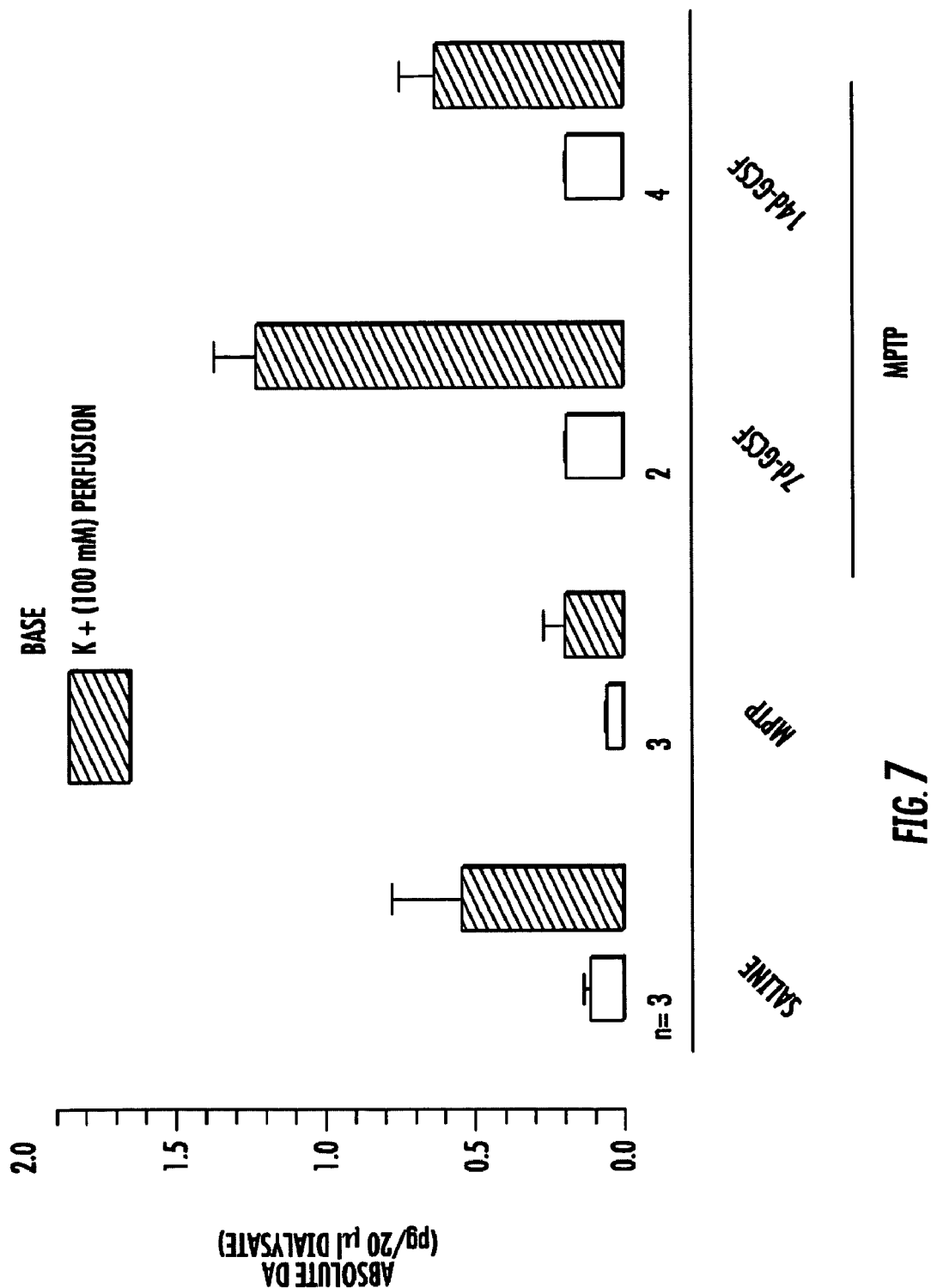
FIG. 7 is a graph showing that G-CSF restores MPTP-induced loss of stimulation-induced release of DA, an index of dopaminergic neural activity.
Figure 8:
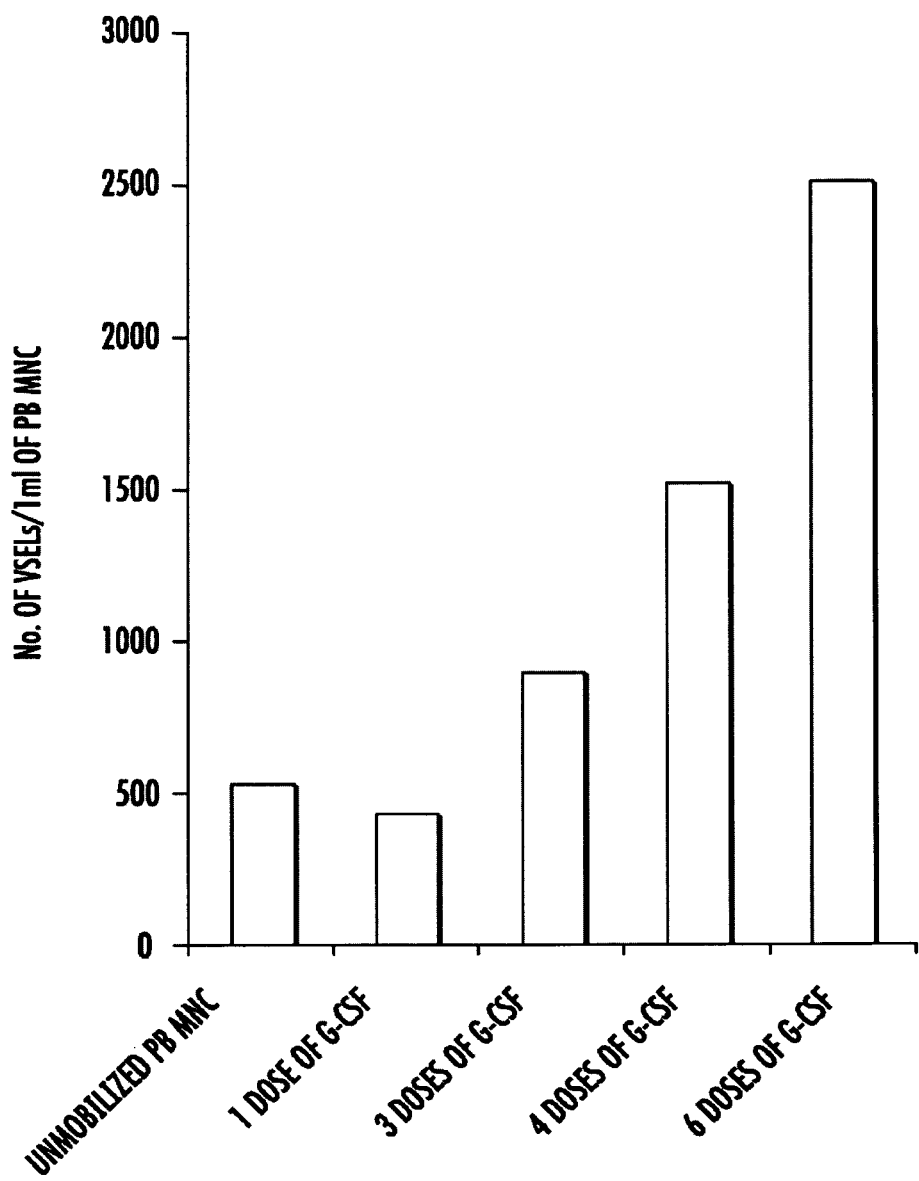
FIG. 8 is a graph showing that G-CSF treatment greatly increased the mobilization of very small embryonic-like cells (VSELs) into peripheral blood in mice. A five-fold increase of mobilization of VSELs was obtained after treatment with 5 doses of G-CSF.
Figure 9:
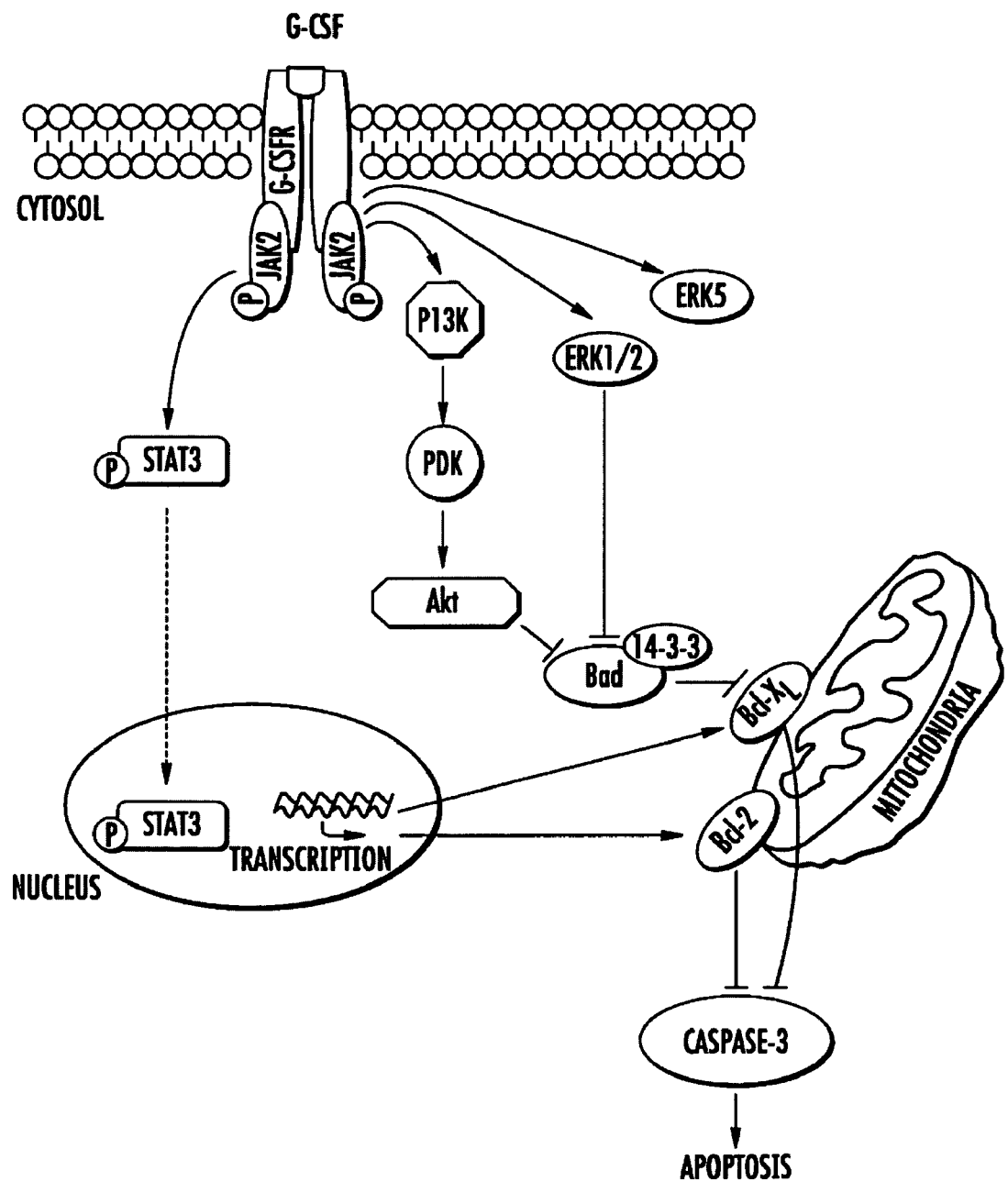
FIG. 9 is a schematic illustration of the G-CSF receptor signaling hypothesis.
Figure 10:
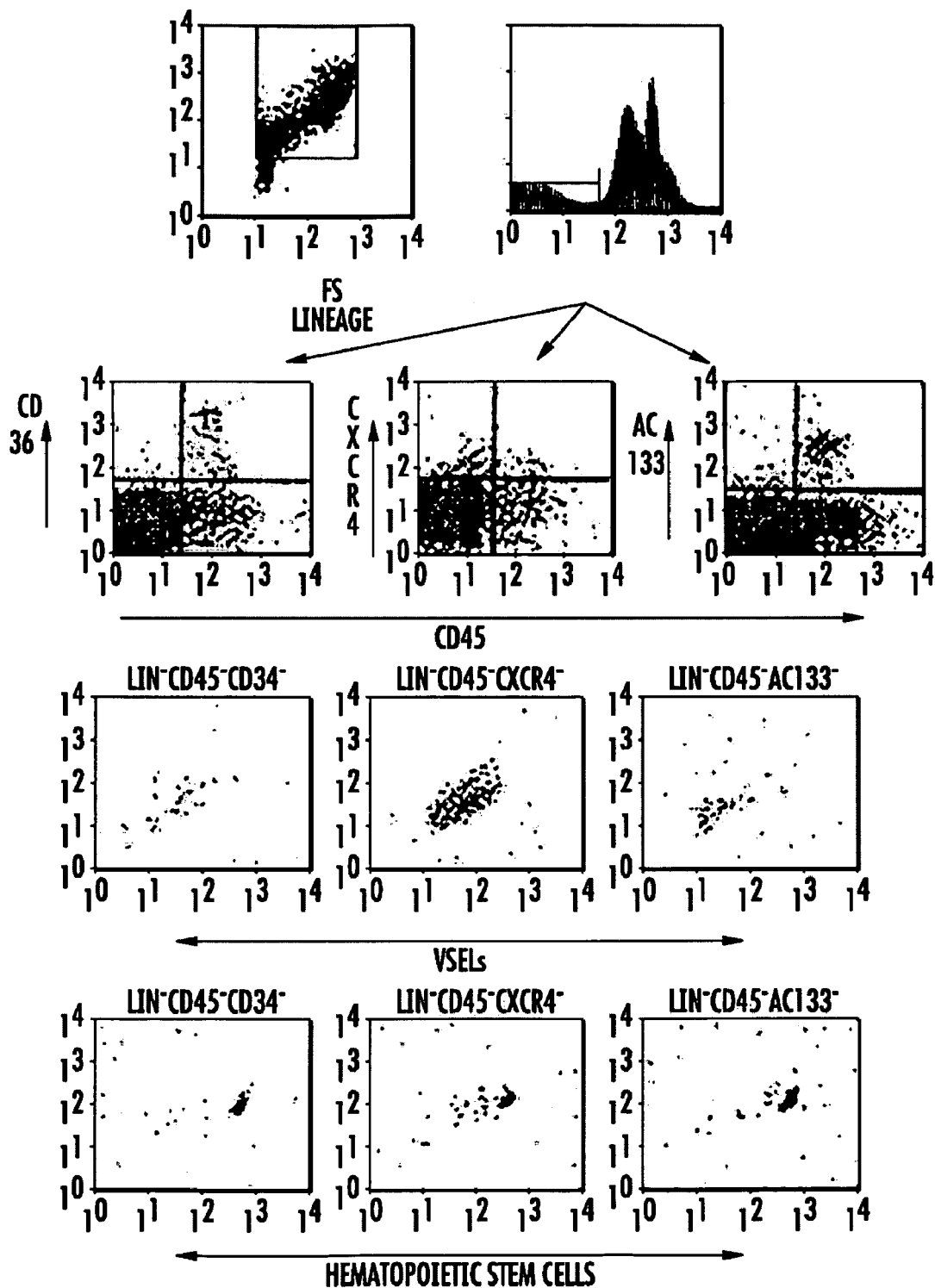
FIG. 10 a graph showing increased mobilization of VSEL stem cells after G-CSF treatment.

FIGS. 5-7 demonstrate the following results: (1) G-CSF treatment increases the number of dopamine neurons in SN in the MPTP-induced PD mouse model as shown in the immunohistochemical staining of TH, a marker for dopamine neurons (FIG. 5); (2) G-CSF treatment partially restores nigrastriatal pathway as shown by retrograde labeling (FIG. 6); and (3) G-CSF restores the function of dopamine neurons as demonstrated in stimulation-induced release of dopamine (FIG. 7). The methods used in these experiments is as follows. Studies were conducted in male C57BL/6 mice (8-10 weeks old; weighing 25-30 g). All surgical procedures were performed according to the guidelines of the Institutional Animal Care and Use Committee (IACUC) at Florida Atlantic University. The mice were divided into 5 groups (n=4, each). The MPTP group of mice were intraperitoneally injected with MPTP-HCL at 30 mg/kg for five consecutive days, and the mice were then allowed one day for recovery followed by subcutaneous injection of equal doses of 5% dextrose instead of G-CSF. The G-CSF treatment group mice were intraperitoneally injected with MPTP-HCL at 30 mg/kg for five consecutive days, and the mice were then allowed one day for recovery followed by subcutaneous injection of G-CSF at 250 μg/kg for seven consecutive days. The control group mice were injected with equal volumes of saline instead of MPTP followed by 5% dextrose instead of G-CSF. Data were collected 1 day, 7 days and 14 days after the last G-CSF injection.

Figure 5A:
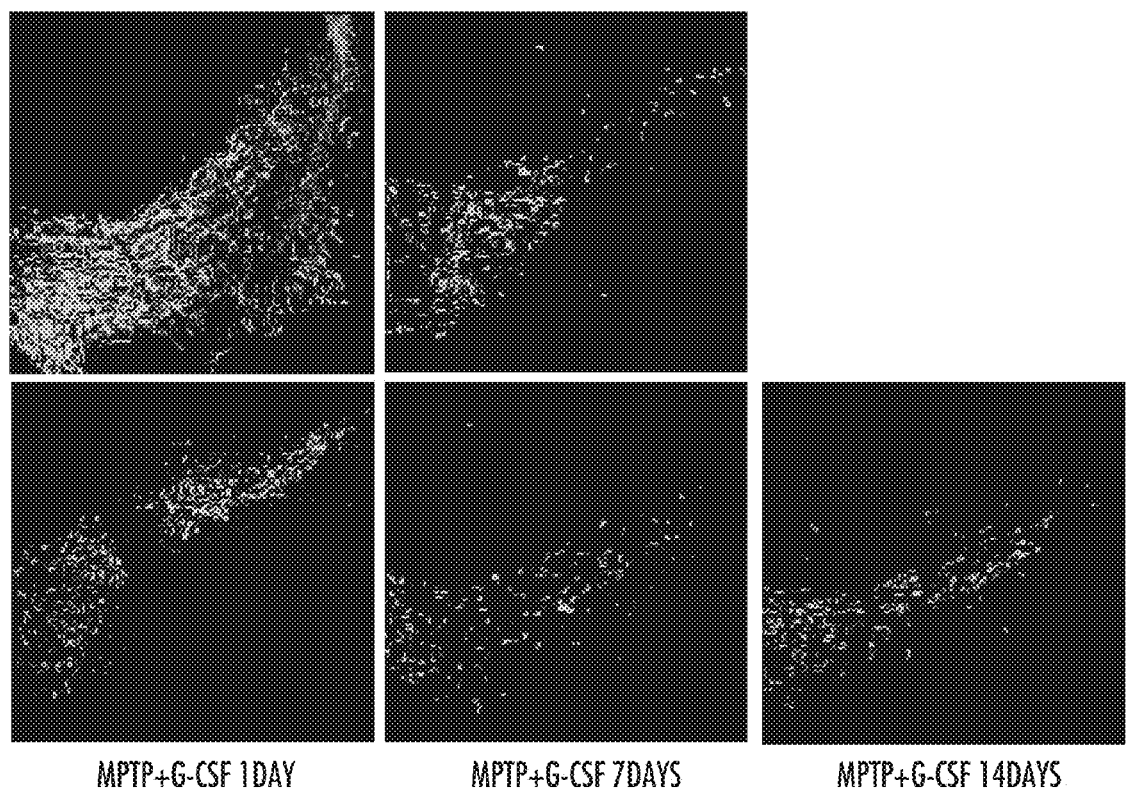
FIG. 5A is a series of representative micrographs depicting TH labeling in the SNc before and after G-CSF treatment as indicated showing that G-CSF treatment partially restores DA neurons as indicated from TH immunolabeling in SNc. G-CSF treatment has increased the number of DA neurons from 45% of the control after MPTP treatment to about 80% in 7 days.
Figure 5B:
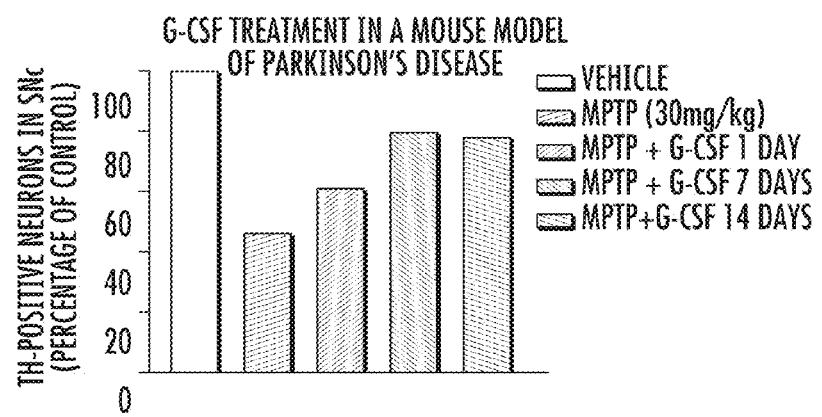
FIG. 5B is a graph showing results from a quantitative analysis of TH-positive cells before and after G-CSF treatment in SNc.

Referring to FIGS. 5A and 5B, FIG. 5A is a series of representative micrographs depicting TH labeling in the SNc before and after G-CSF treatment as indicated showing that G-CSF treatment partially restores DA neurons in indicated from TH immunolabeling in SNc. G-CSF treatment has increased the number of DA neurons from 45% of the control after MPTP treatment to about 80% in 7 days. FIG. 5B is a graph showing results from a quantitative analysis of TH-positive cells before and after G-CSF treatment in SNc.

Referring to FIGS. 6A and 6B, G-CSF treatment restored the nigrastriatal pathway in mice. In these experiments, mice received unilateral intrastriatal infusion of the retrograde fluorescent tracer FG into two sites in the striatum at a rate of 0.05 μl/min five days before being killed. FIG. 6A is a series of representative micrographs depicting FG labeling in the SN 14 days after 5% dextrose+MPTP (top panel) or 5% dextrose+MPTP+G-CSF treatment (bottom panel) showing that G-CSF treatment has restored the nigro-striatum pathway from 40% to 70% as indicated in FG-positive tracing. FIG. 6B is a graph showing the results of a quantitative analysis of FG-positive cells counted across 8 sections throughout SN. *$p<0.01$.

Referring to FIG. 7, G-CSF normalizes MPTP-induced loss of dopaminergic neural activity. Experiments were carried out using microdialysis of dopamine release in the SN.

As compared to the vehicle treatment, injection of MPTP caused a reduction in basal release of dopamine. Additionally, the increase in dopamine release induced by high potassium stimulation (100 mM for 20 min) were also decreased, suggesting that dopaminergic neural function was impaired. After treatment with G-CSF, the basal release was improved as compared to the MPTP group. Dopamine response to potassium stimulation was restored to that in the vehicle level.

Example 2

Mechanism and Therapy of G-CSF in a Patient with PD

Figure 11:
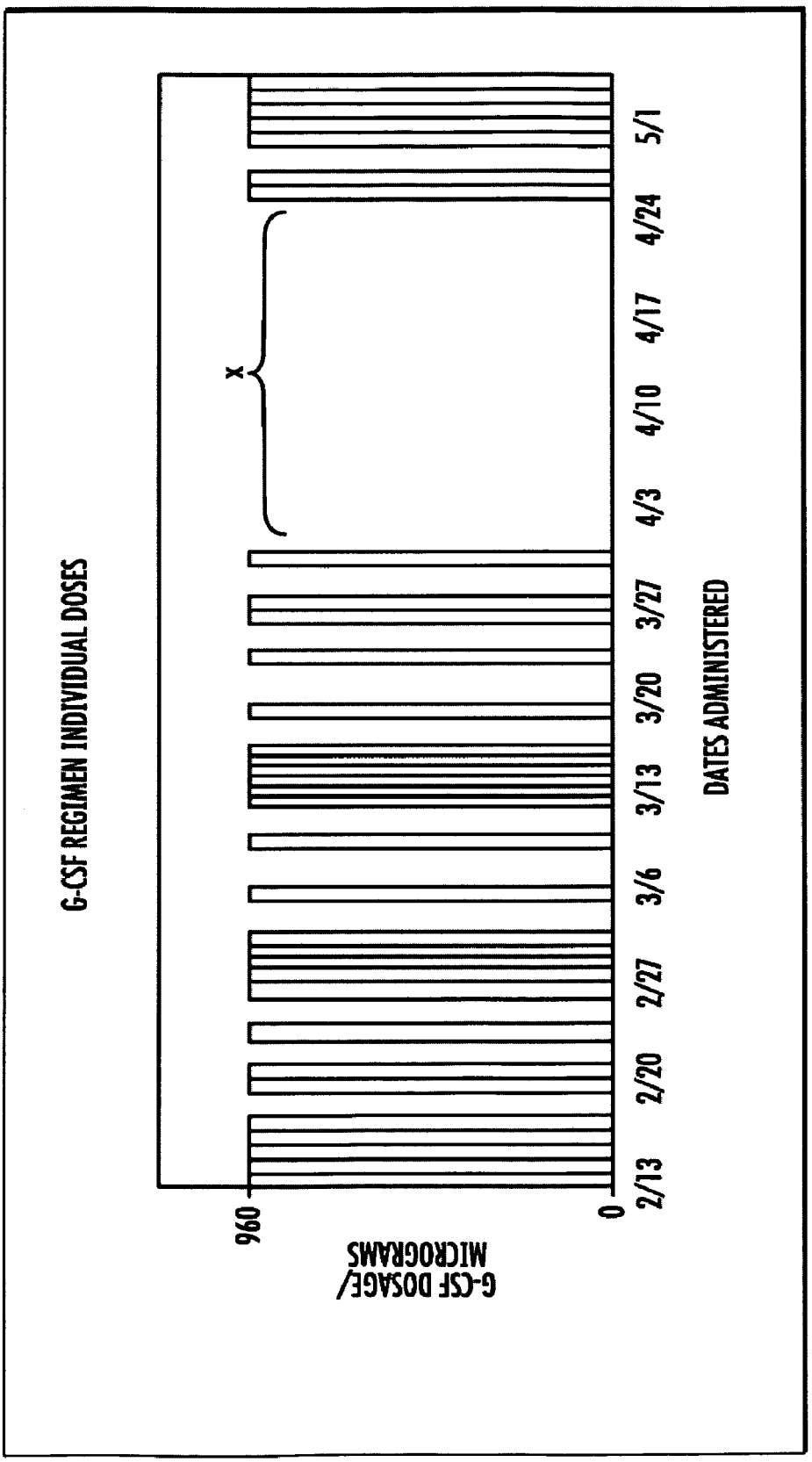
FIG. 11 is a graph of G-CSF regimen individual doses.

A patient with corticobasilar ganglionic degeneration, a rare progressive neurological disorder characterized by Parkinsonism and cortical dysfunction, was treated with a daily subcutaneous dose of 960 µg of G-CSF in order to mobilize stem cells continuously for 7 days followed by a rest period of 7 days. This cycle of treatment was repeated for a total of 5 cycles. (FIG. 11). UPDRS evaluations before and after treatment showed a significant (about 60%) improvement, as did measures of activities of daily living.

Referring to FIG. 11, the G-CSF regimen included a daily subcutaneous dose 960 µg of G-CSF continuously for 7 days followed by a rest period of 7 days (1 cycle). This cycle of treatment was repeated for a total of 4 cycles.

Figure 12B:
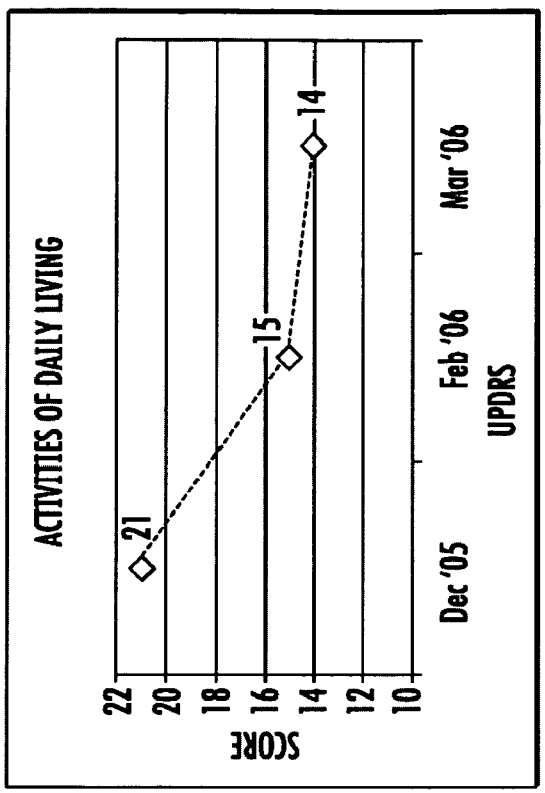
FIG. 12B is a graph depicting activities of daily living UPDRS scores after G-CSF treatment.
Figure 12A:
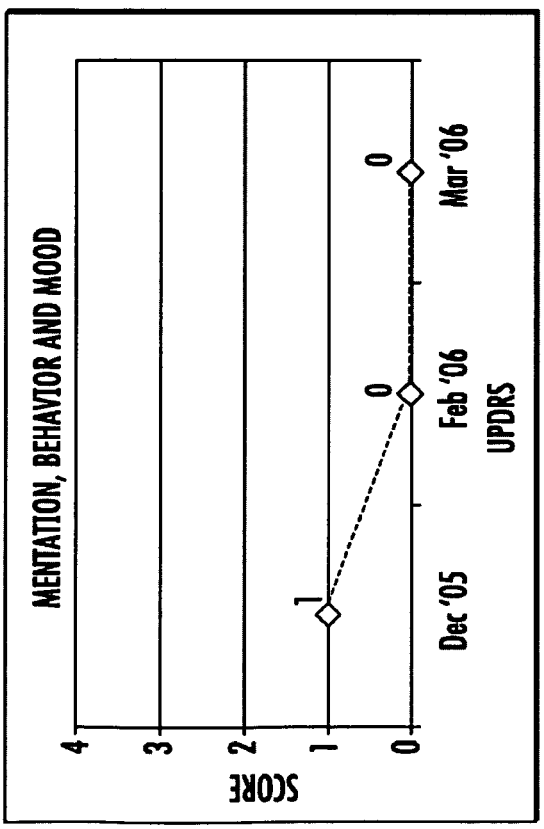
FIG. 12A is a graph depicting mentation, behavior and mood UPDRS scores after G-CSF treatment.
Figure 13B:
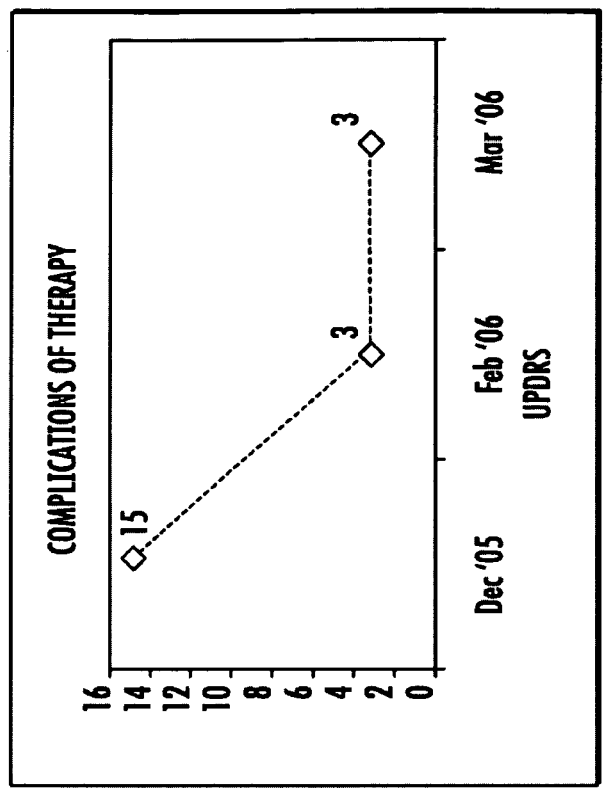
FIG. 13B is a graph depicting complications of therapy UPDRS scores after G-CSF treatment.
Figure 13A:
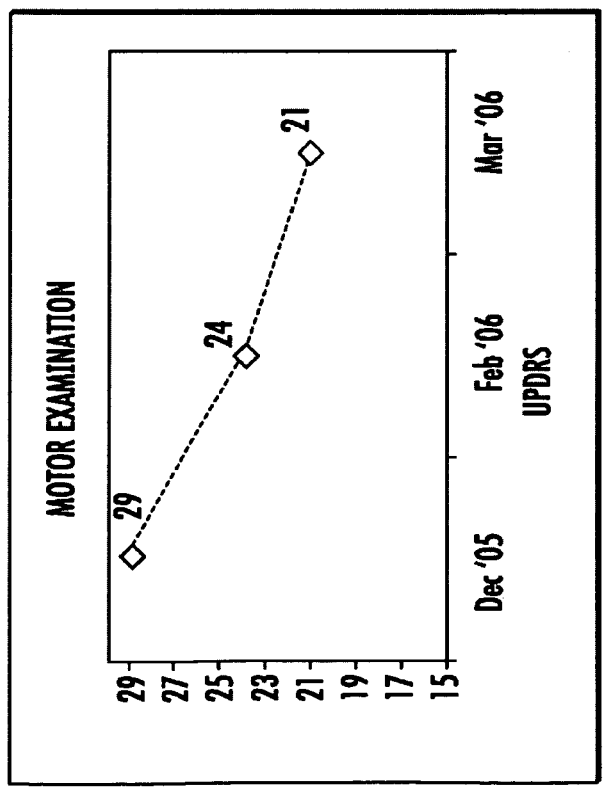
FIG. 13A is a graph depicting motor examination UPDRS scores after G-CSF treatment.

FIGS. 12 and 13 show UPDRS scores for the patient. Table 1 lists the UPDRS scores. In FIG. 12, UPDRS scores for mentation, behavior and mood (FIG. 12A) and activities of daily living (FIG. 12B) are shown. For mentation and behavior in FIG. 12A, there was an overall improvement of one (1) on the score specifically related to improvement in depression. For activities of daily living in FIG. 12B, there was a remarkable overall improvement of seven (7) in the UPDRS score. In FIG. 13A, motor examination showed an overall improvement of eight (8) in the score. In FIG. 13B, the complications of therapy aspect of the scale showed the most improvement with a reduction of 12 in the UPDRS score.

TABLE 1

Unified Parkinson's Rating Scores

|  | month 1 | month 2 | month 3 |
| --- | --- | --- | --- |
| MENTATION, BEHAVIOR AND MOOD | | | |
| Intellectual Impairment | 0 | 0 | 0 |
| Thought Disorder | 0 | 0 | 0 |
| Depression | 1 | 0 | 0 |
| Motivation/Initiative | 0 | 0 | 0 |
| ACTIVITIES OF DAILY LIVING | | | |
| Speech | 1 | 1 | 1 |
| Salivation | 0 | 0 | 0 |
| Swallowing | 0 | 0 | 0 |
| Handwriting | 4 | 4 | 4 |
| Cutting food and handling utensils | 4 | 3 | 3 |
| Dressing | 4 | 2 | 2 |
| Hygiene | 3 | 3 | 3 |
| Turning in bed and adjusting bed clothes | 1 | 0 | 0 |
| Falling (unrelated to freezing) | 0 | 0 | 0 |
| Freezing when walking | 0 | 0 | 0 |
| Walking | 2 | 0 | 0 |
| Tremor | 1 | 1 | 1 |
| Sensory complaints related to parkinsonism | 1 | 1 | 0 |
| MOTOR EXAMINATION | | | |
| Speech | 1 | 2 | 1 |
| Facial Expression | 2 | 2 | 0 |
| Tremor at rest | 1 | 1 | 1 |
| Action or Postural Tremor of hands | 2 | 2 | 2 |
| Rigidity | 4 | 4 | 4 |
| Finger Taps | 4 | 4 | 4 |
| Hand Movements | 3 | 2 | 2 |
| Rapid Alternating Movements of Hands | 4 | 3 | 3 |
| Leg Agility | 1 | 1 | 1 |
| Arising from Chair | 1 | 0 | 0 |
| Posture | 1 | 0 | 0 |
| Gait | 1 | 1 | 1 |
| Postural Stability | 1 | 0 | 0 |
| Body Bradykinesia and Hypokinesia | 3 | 2 | 2 |
| COMPLICATIONS OF THERAPY (In the past week) | | | |
| A. DYSKINESIAS | | | |
| Duration: What proportion of the waking day are dyskinesias present? | 4 | 1 | 1 |
| Disability: How disabling are the dyskinesias? | 3 | 1 | 1 |
| Painful Dyskinesias: How painful are the dyskinesias? | 2 | 0 | 0 |
| Presence of Early Morning Dystonia | 1 | 0 | 0 |
| B. CLINICAL FLUCTUATIONS | | | |
| Are "off" periods predictable? | 0 | 0 | 0 |
| Are "off" periods unpredictable? | 0 | 0 | 0 |
| Do "off" periods come on suddenly, within a few seconds? | 0 | 0 | 0 |
| What proportion of the waking day is the patient "off" on average? | 4 | 1 | 1 |
| C. OTHER COMPLICATIONS | | | |
| Does the patient have anorexia, nausea, or vomiting? | 0 | 0 | 0 |
| Any sleep disturbances, such as insomnia or hypersomnolence? | 1 | 0 | 0 |
| Does the patient have symptomatic orthostasis? | 0 | 0 | 0 |
| Total | 66 | 42 | 38 |

Example 3

The Effect of G-CSF on Mobilization of VSEL in PD Patients

In a planned clinical trial, peripheral blood samples of each patient is taken prior to initiation of G-CSF treatment for assessment of baseline VSEL numbers (at the SFBMSCII). Patients are then treated with G-CSF at FDA-approved mobilization doses for either one or three cycles. Each cycle entails daily G-CSF dosing for five days and a subsequent nine day G-CSF free period required for bone marrow recovery. Peripheral blood samples are collected daily for complete blood count monitoring of safety and efficacy of G-CSF treatment and samples are analyzed by FACS and molecular analyses for VSEL populations. VSEL populations are analyzed by molecular analysis.

A planned Phase II safety and dosing-range study of G-CSF in PD is performed. In this double-blind proof-of-concept trial, patients are equally randomized to either one course or three courses of this therapy. Thirty patients are enrolled in this pilot study, with the goal of twenty patients completing therapy. Patients are eligible for enrollment if they are Hoehn and Yahn stage 3 when off medication and also experience troublesome peak dose dyskinesia. Two primary endpoints are measured: (1) safety and tolerability of G-CSF in PD; and (2) presence of VSEL populations in the peripheral circulation after one vs. three cycles of G-CSF. Secondary endpoints of clinical efficacy are also measured. The following analyses are performed: (1) assess safety and patient tolerability of G-CSF in patients with PD; (2) use flow cytometry to detect VSEL populations in the peripheral blood circulation after G-CSF treatment; (3) assess the effect on clinical efficacy (using Hoehn & Yahn Stage, UPDRS, Mini Mental State Examination, Neuropsychiatric Inventory, Non-Motor Assessment, Schwab & England ADL, PDQ-39 Quality of Life, Epworth Sleepiness Scale, Beck Depression Inventor, Beck Anxiety Inventory); (4) study a sub-group of patients before and after G-CSF treatment with neuroimaging (fluorodopa-PET and/or β-CIT-SPECT).

Patients are eligible for enrollment in a planned Phase III study evaluating efficacy and potential disease-modifying effects of G-CSF in PD if they are Hoehn and Yahr stage 3 when off medication and also experience troublesome peak dose dyskinesia. Using the G-CSF dosing scheme identified in the initial phase II trial, patients are randomized 2:1 to G-CSF treatment or placebo. Patients will be evaluated for clinical efficacy (using above scales), neuroimaging (fluorodopa-PET and/or β-CIT-SPECT), and flow cytometry for VSEL populations in the peripheral blood circulation. These assessments are compared to baseline during and after G-CSF treatment, and subjects will also be followed over a two-year period to evaluate possible emergence of delayed treatment effects, including improvement in OFF stage (i.e., improved postural reflexes) and reduction of motor fluctuations (i.e. OFF time and/or troublesome peak dysinesia).

Example 4

Treatment of a Stroke Patient with G-CSF

A male patient who had suffered a stroke experienced an improvement in his stroke symptoms while receiving G-CSF treatment. The patient developed a pontine infarct of sudden onset. This was diagnosed after he developed symptoms of dysarthria, ataxia and dysphagia. The stroke which was due to a pontine infarct was demonstrated on an MRI scan. He had swallowing studies done as well as carotid doppler studies. He was treated with a daily subcutaneous dose 480 μg of G-CSF in order to mobilize stem cells continuously for 14 days. The patient's speech returned to normal and although he still had difficulty walking there was a significant improvement in his walking. He was also able to eat normally. The patient has minimal observable disability six years later.

Other Embodiments

Any improvement may be made in part or all of the kits and method steps. All references, including publications, patent applications, and patents, cited herein are hereby incorporated by reference. The use of any and all examples, or exemplary language (e.g., "such as") provided herein, is intended to illuminate the present disclosure and does not pose a limitation on the scope of the invention unless otherwise claimed. Any statement herein as to the nature or benefits of the present disclosure or of the preferred embodiments is not intended to be limiting, and the appended claims should not be deemed to be limited by such statements. More generally, no language in the specification should be construed as indicating any non-claimed element as being essential to the practice of the invention.

The invention claimed is:

1. A method of treating Parkinson's disease in a mammal, the method comprising the steps of:
    (a) providing a composition comprising recombinant human G-CSF; and
    (b) administering the composition to a mammalian subject having Parkinson's disease at a daily dose of about 960 μg of G-CSF for seven consecutive days followed by seven days of no G-CSF administration; and
    (c) repeating step (b) four more times, wherein administering the composition to the mammalian subject replenishes dopaminergic neuron loss in the brain of the mammalian subject and mobilizes stem cells into peripheral blood of the mammal.

2. The method of claim 1, wherein administering the composition to the mammalian subject results in increased levels of dopaminergic neurons and increased levels of dopaminergic neuronal function in the brain of the mammalian subject.

3. The method of claim 1, wherein administering the composition to the mammalian subject results in restoration of nigrostriatal pathway in the brain of the mammalian subject.

4. The method of claim 1, wherein administering the composition to the mammalian subject results in recruitment of stem cells to the brain of the mammalian subject.

5. The method of claim 1, wherein the composition comprises at least one pharmaceutically acceptable carrier or diluent.

6. The method of claim 1, wherein the mammalian subject has advanced Parkinson's disease.

7. The method of claim 1, wherein the mammalian subject is a human.

8. The method of claim 7, wherein administration of the composition results in about a 60% improvement in the mammalian subject based on United Parkinson's Disease Rating Score (UPDRS).

* * * * *